(12) United States Patent
Tachibana

(10) Patent No.: US 6,269,143 B1
(45) Date of Patent: Jul. 31, 2001

(54) RADIOTHERAPY PLANNING SYSTEM

(75) Inventor: Kazushige Tachibana, Ibaraki (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/383,013

(22) Filed: Aug. 25, 1999

(30) Foreign Application Priority Data

Aug. 31, 1998 (JP) .................................................. 10-245680

(51) Int. Cl.[7] .................................................. A61N 5/10
(52) U.S. Cl. .................................................. 378/65; 378/20
(58) Field of Search .................................. 378/65, 64, 4, 378/20, 193, 195, 196, 208, 209

(56) References Cited

U.S. PATENT DOCUMENTS

| | | | |
|---|---|---|---|
| 5,039,867 | * 8/1991 | Nishihara et al. | 378/205 X |
| 5,206,893 | * 4/1993 | Hara | 378/65 |
| 5,297,037 | * 3/1994 | Ifuku | 378/65 X |
| 5,329,567 | * 7/1994 | Ikebe | 378/20 |
| 5,533,082 | * 7/1996 | Gronemeyer et al. | 378/20 |
| 5,901,199 | * 6/1999 | Murphey et al. | 378/65 |
| 6,032,066 | * 2/2000 | Lu et al. | 378/65 X |

* cited by examiner

Primary Examiner—David P. Porta
(74) Attorney, Agent, or Firm—Arent Fox Kintner; Plotkin & Kahn, PLLC

(57) ABSTRACT

A simulated image is produced from image data acquired from a CT simulator, and an irradiation field shape and a irradiation center are set on the simulated image. The irradiation field shape set is displayed as superposed on a fluoroscopic image of a patient photographed by an X-ray simulator with an X-ray tube and a flat panel imaging system for medical X ray.

12 Claims, 5 Drawing Sheets 51 sectional image simulation image 52
55 isocenter
54 field shape
53 diseased part image

RADIOTHERAPY PLANNING SYSTEM

BACKGROUND OF THE INVENTION

(1) Field of the Invention

This invention relates to a radiotherapy planning system for making a treatment plan, such as determining an irradiation field shape, in advance of treating disease such as cancer with radiation.

(2) Description of the Related Art

In treating disease such as cancer with radiation, the diseased part must be irradiated properly. For this purpose, a radiotherapy planning system is used to acquire images of and around the diseased part by means of an X-ray CT apparatus and a fluoroscopic apparatus, and to determine an irradiation field shape coinciding with an outline of an image of the diseased part appearing in an image acquired.

Such a radiotherapy planning system often includes a CT simulator and an X-ray simulator. The CT simulator has an X-ray CT apparatus as a main component thereof, while the X-ray simulator has an X-ray TV apparatus as a main component thereof. These simulators have certain additional functions, respectively. First, CT radiography is carried out using the CT simulator to acquire a plurality of sectional images. These sectional images are combined to reproduce a three-dimensional image, and then an oblique image (transmitted image seen from one direction) is produced therefrom. Alternatively, CR images which are fluoroscopic images are photographed by linearly moving a CT detector. These simulation images are displayed to identify a diseased part to be treated.

Next, an irradiating angle is determined from sectional images of a wide region including the diseased part or a transmitted image, seen from a particular direction, produced from a three-dimensional image obtained by combining the sectional images. A transmitted image seen from the irradiating angle is displayed. Then, the operator determines a shape of an irradiation field on the image displayed, and sets an isocenter to the irradiation field. Further, a position corresponding to the isocenter is marked on the patient's surface (skin surface).

Subsequently, the patient is positioned relative to the X-ray simulator by using the mark on the skin surface as a reference, so that the mark coincides with the isocenter of the X-ray simulator. An X-ray irradiating angle corresponding to the irradiating angle determined as above is set to the X-ray simulator, and an image is photographed on a film through radiography for use as a reference photograph for collation.

Further, the patient is positioned relative to a radiation treating apparatus by using the mark on the skin surface as a reference, so that the mark coincides with the isocenter of the treating apparatus. An irradiating angle is set to the irradiating angle determined as above, and film radiography is carried out by emitting radiation. This radiation film image is collated with the above X-ray film image acting as the reference photograph to confirm that the patient has been positioned according to plan.

After this is confirmed, radiotherapy is performed for the diseased part by actually emitting radiation from the radiation treating apparatus.

However, the conventional radiotherapy planning system has a drawback of not always assuring a treatment plan made for irradiating a diseased part with an appropriate irradiation field shape.

That is, in the conventional system, an oblique image or the like produced from sectional images acquired from the CT simulator is a still picture, and therefore cannot accurately reflect in the treatment plan the movement of internal organs and the like due to respiration and other functions. Further, fluoroscopic images are conventionally acquired with the X-ray simulator using an image intensifier. The fluoroscopic images acquired are distorted by curvature of the X-ray incidence surface. When an irradiation field shape is verified on a fluoroscopic image, the field shape fails to exhibit a reliable geometrical conformity to the actual diseased part.

SUMMARY OF THE INVENTION

This invention has been made having regard to the state of the art noted above, and its object is to provide an improved radiotherapy planning system for properly making an irradiation field shape for radiation treatment according to an actual shape of a diseased part.

The above object is fulfilled, according to this invention, by a radiotherapy planning system for making a treatment plan for radiation treatment, comprising:

a CT simulator including a CT image pickup gantry having an X-ray tube and an X-ray detecting device, a pointer for indicating an irradiation center, and a patient supporting device;

an X-ray simulator including an X-ray tube, a flat panel imaging system for medical X ray and a patient supporting device;

a setting device for setting an irradiation field shape and an irradiation center on an image acquired from the CT simulator; and a superposing and displaying device for displaying a fluoroscopic image acquired from the X-ray simulator, with the irradiation field shape superposed thereon.

With this construction, a fluoroscopic image acquired from the X-ray simulator is displayed with, superposed thereon, an irradiation field shape determined beforehand. Thus, the validity of the field shape may be checked by using the fluoroscopic image. The fluoroscopic image, which is acquired from the flat panel imaging system for medical X ray, is free from distortion and has a high degree of geometrical conformity to the image acquired from the CT simulator. The fluoroscopic image is superior in image quality to the image acquired from the CT simulator, and may be displayed as a dynamic image. By using the fluoroscopic image having such features, the field shape may be checked easily and accurately. Even when the site to be treated has moved with the patient's movement, an appropriate field shape may be determined by taking such movement into account since the operator can observe the dynamic image.

The image collecting system in the X-ray simulator consists only of the light and small flat panel imaging system for medical X ray. There is no need to use a heavy and bulky combination of an image intensifier and a TV camera used in the prior art. Thus, without requiring a support structure of great strength, fluoroscopic images may be picked up from varied angles with enhanced geometrical precision such as precision in imaging angle. The X-ray simulator, though having a simplified and inexpensive construction, can provide fluoroscopic images with increased accuracy. Consequently, while achieving economy, the field shape may be checked accurately and properly by using fluoroscopy.

In the above radiotherapy planning system, the setting device and the superposing and displaying device may comprise a computer. With this construction, the setting device and the superposing and displaying device are realized in a simple way, and the system may be downsized and simplified.

Images acquired from the CT simulator and images acquired from the X-ray simulator may be processed by one computer.

With this construction, a treatment plan may be made efficiently while operating the computer to display each of the images acquired from the CT simulator and X-ray simulator.

In the above radiotherapy planning system, one patient supporting device may be shared by the CT simulator and X-ray simulator.

This construction has a reduced number of components to achieve compactness and low cost of the system. The two simulators can pick up images of the patient supported on the one patient supporting device. The patient need not be placed on or removed from the patient supporting device while picking up images necessary to make a treatment plan. There is a reduced chance of variations in patient's position relative to the patient supporting device, which facilitates positional adjustment of the patient to each simulator.

Where one patient supporting device is shared by the two simulators, the CT simulator and X-ray simulator may be arranged around the one patient supporting device which is pivotable about a support axis. Thus, with the patient directed to the CT simulator by turning the one patient supporting device about the support axis, an operation (e.g. sectional image pickup) may be performed by actuating the CT simulator. When the patient is directed to the X-ray simulator, an operation (e.g. fluoroscopic image pickup) may be performed by actuating the X-ray simulator.

In the above radiotherapy planning system, the patient supporting device of the CT simulator and the patient supporting device of the X-ray simulator may be separate. This construction achieves an increased freedom of equipment installation such that the CT simulator and X-ray simulator may be installed in separate rooms.

In the above radiotherapy planning system, the CT simulator may further include a projecting device for emitting to the patient light of the irradiation field shape set by the setting device.

Then, the field shape set may be marked accurately on the patient's skin surface.

The X-ray simulator may also include a pointer for indicating an irradiation center. Then, the irradiation center of the X-ray simulator may be positioned accurately to coincide with the irradiation center determined.

The radiotherapy planning system may further comprise a correcting device for correcting the irradiation field shape set by the setting device, on the fluoroscopic image acquired from the X-ray simulator.

With this construction, the field shape set by the setting device may be verified on the fluoroscopic image acquired from the X-ray simulator, and may be corrected to an appropriate field shape as necessary.

In addition, the radiotherapy planning system may comprise a confirmation-aiding superposing and displaying device for displaying the fluoroscopic image acquired from the X-ray simulator, with, superposed thereon, the irradiation field shape corrected by the correcting device. Then, the field shape corrected by the correcting device may be reconfirmed on the image acquired from the CT simulator. Consequently, the validity of the field shape may be verified with increased reliability.

The correcting device and confirmation-aiding superposing and displaying device may comprise a computer. Then, the correcting device and confirmation-aiding super-8 posing and displaying device are realized in a simple way, and the system may be downsized and simplified.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENTS

A preferred embodiment of this invention will be described in detail hereinafter with reference to the drawings.

Figure 1:
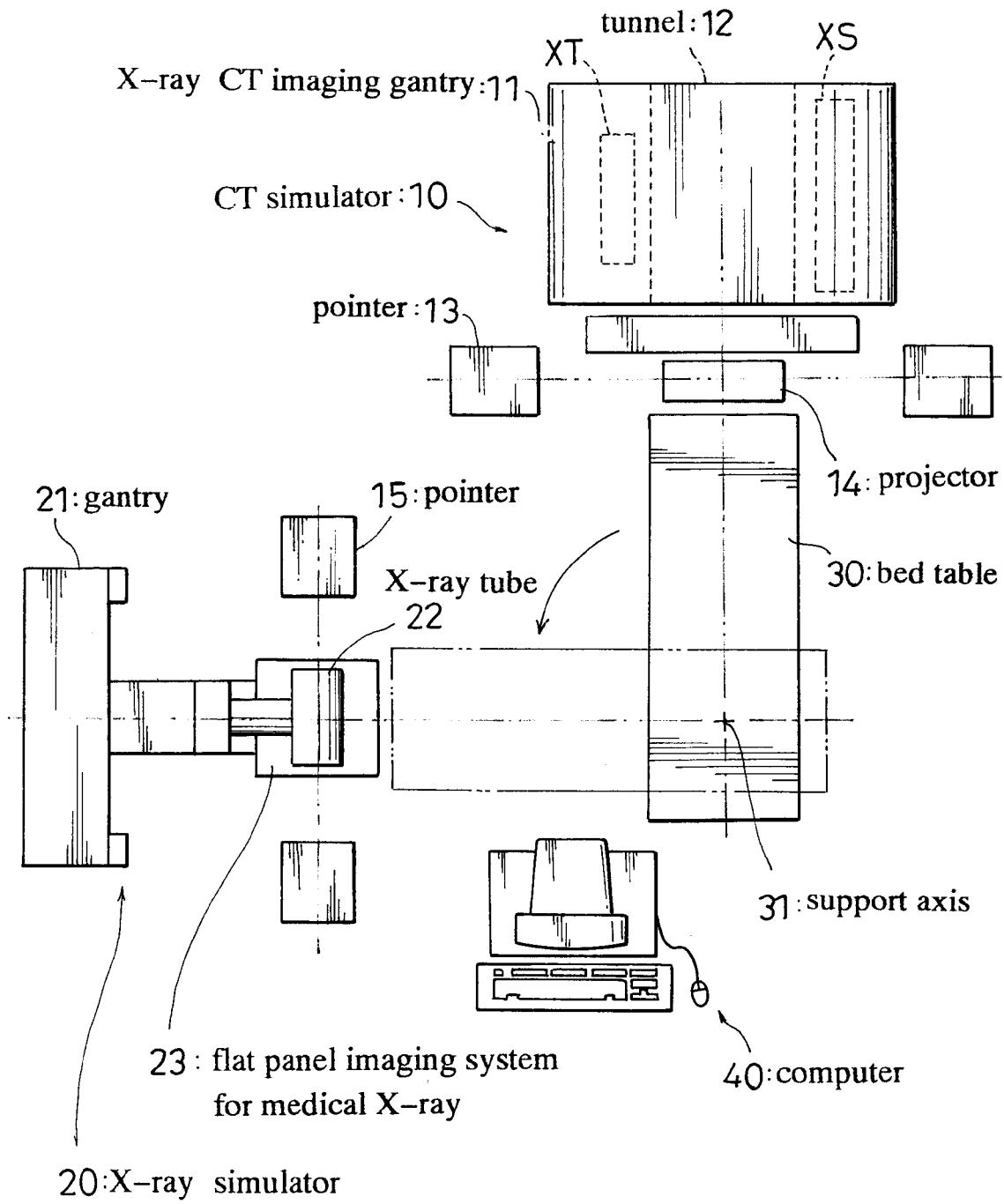
FIG. 1 is a schematic plan view of an embodiment of this invention.

As shown in FIG. 1, a radiotherapy planning system according to this invention includes a CT simulator 10, an X-ray simulator 20, a bed table 30 corresponding to the patient supporting device, and a computer 40. The computer 40 has functions of the setting device, superimposing and displaying device, correcting device and confirmation-aiding superposing and displaying device. The CT simulator 10 includes an X-ray CT imaging gantry 11 with an X-ray tube XT and an X-ray detector (X-ray detecting device) XS disposed therein. A rotating mechanism not shown revolves these X-ray tube XT and X-ray detector XS, as opposed to each other, circumferentially of a tunnel 12. With this rotation, X-ray projection data are acquired from various angular directions. These data are used to reconstruct a sectional image in the plane of rotation of the X-ray tube XT and X-ray detector XS.

Figure 4:
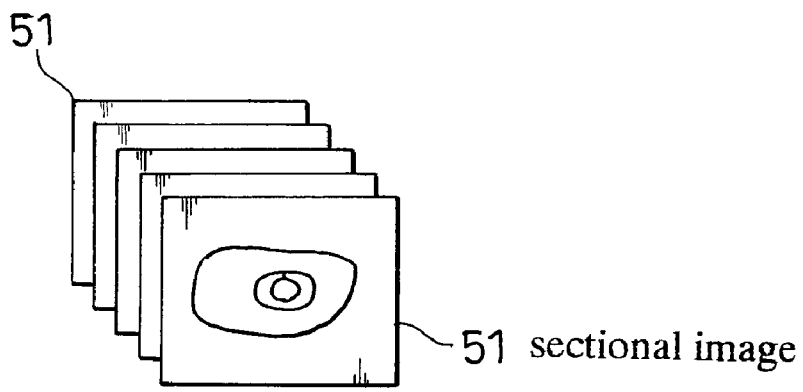
FIG. 4 view showing a plurality of sectional images picked up by a CT simulator.

A patient 32 is placed on the bed table 30 and inserted into the tunnel 12 for acquiring sectional images transversely of his or her body axis. The bed table 30 is moved forward or backward in the tunnel 12. Data of transmitted X ray is acquired, thereby acquiring a plurality of sectional images 51 transversely of the body axis as shown in FIG. 4.

The CT simulator 10 further includes a pointer 13 for indicating an isocenter serving as the center of irradiation, and a projector 14 corresponding to the projecting device for emitting light beams having a field shape determined to the surface (skin surface) of patient 32. The projector 14 is revolvable about the body axis of patient 32 to emit light from selected directions.

Figure 2:
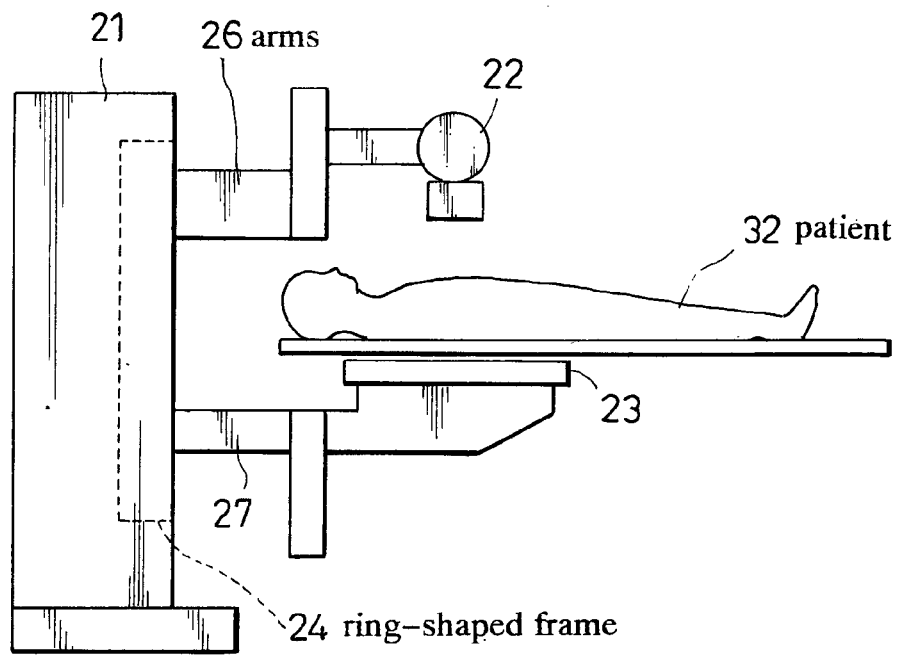
FIG. 2 is a side view of an X-ray simulator in the embodiment of this invention.
Figure 3:
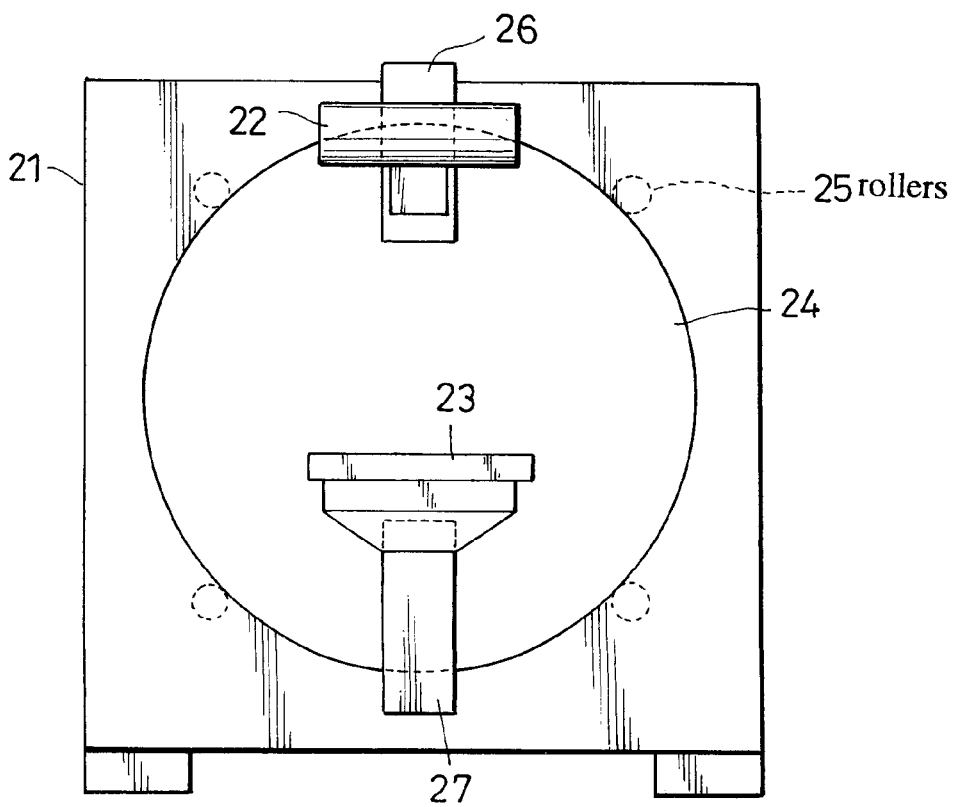
FIG. 3 is a front view of the X-ray simulator.

The X-ray simulator 20 includes an X-ray tube 22 and a flat panel imaging system for medical X ray 23. As shown also in FIGS. 2 and 3, the X-ray tube 22 and flat panel imaging system for medical X ray 23 are mounted on arms 26 and 27 extending from a ring-shaped frame 24 supported in a gantry 21. The ring-shaped frame 24 is rotatably supported through rollers 25 or the like. The X-ray tube 22 irradiates the patient 32 with X rays from a selected angle, whereby the flat panel imaging system for medical X ray 23 acquires signals of a fluoroscopic image from the selected angle. The X-ray simulator 20 also includes a pointer 15 as does the CT simulator 10.

In this embodiment, the bed table 30 is pivotable about a support axis 31 to be shared by the CT simulator 10 and X-ray simulator 20. The computer 40 receives image data from the CT simulator 10 and X-ray simulator 20, and processes these data for display on a display 41 (see FIG. 6).

Figure 5:
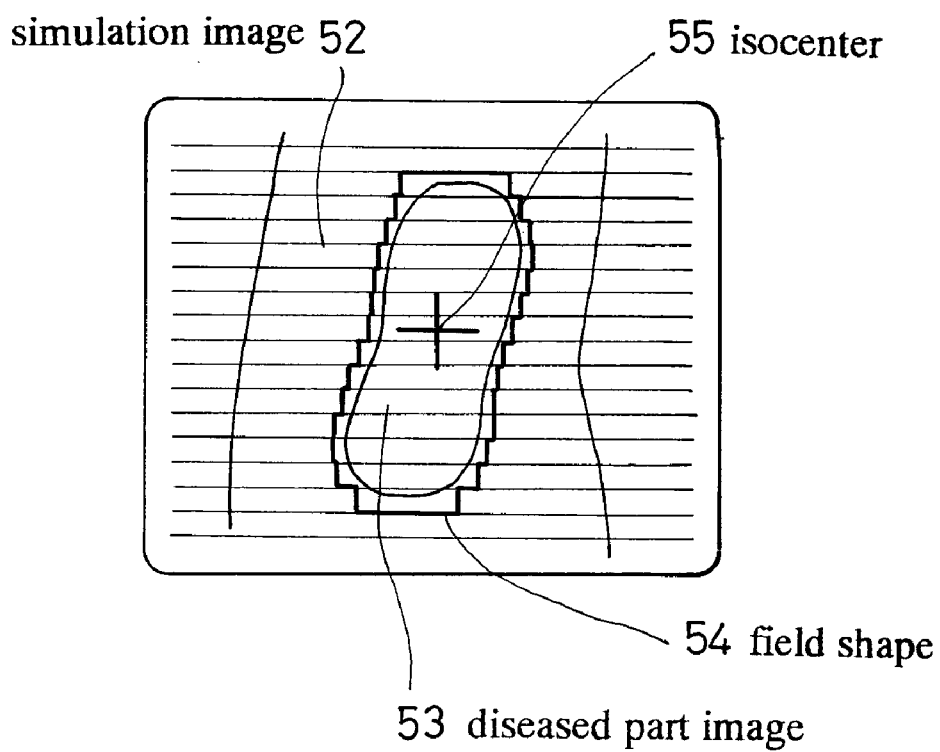
FIG. 5 is a view showing an isocenter and a field shape appearing on a simulated image.

When the CT simulator 10 acquires a plurality of sectional images 51 transversely of the body axis of patient 32 (see FIG. 4), the image data are transmitted to the computer 40. The computer combines these sectional images to produce transmitted images (oblique images or the like) seen from selected directions. As shown in FIG. 5, simulation images 52 made in this way are displayed on the screen of display 41. The operator observes images of a diseased part 53 from various directions. Then, based on appearance of the diseased part images 53, the operator selects a simulation image 52 seen from a particular direction, and sets an isocenter 55 to the center of the diseased part image 53 by regarding that direction as an irradiating direction. Further, the operator determines an irradiation field shape 54 appropriately enclosing the diseased part image 53. The operator performs these operations by operating a mouse or the like while looking at the display 41.

The position of isocenter 55 set to the simulation image 52 corresponds to a position on the plane of the particular sectional image 51. When the field shape 54 and isocenter 55 are determined on the computer 40 as noted above, the bed table 30 is moved to a position for the pointer 13 to indicate the isocenter 55. Then, the projector 14 is revolved to the same angle as the simulation image 52, and light beams corresponding in shape to the field shape 54 determined as above are emitted from the projector 14 to the patient 32. These operations are performed under control of the computer 40. In this way, the field shape 54 is marked on the actual skin surface of patient 32, and a mark corresponding to the isocenter 55 is applied to the skin surface of patient 32 based on the indication by the pointer 13.

Next, the bed table 30 is turned about the support axis 31 to extend toward the X-ray simulator 20. Then, the bed table 30 is moved to a position where the mark applied to the patient 32 coincides with the center of irradiation. Unless the patient 32 moves on the bed table 30, this positioning may be achieved by automatically moving the bed table 30. Even when the patient 32 has moved, similar positioning is possible by using the pointer 15 to apply a mark.

Figure 6:
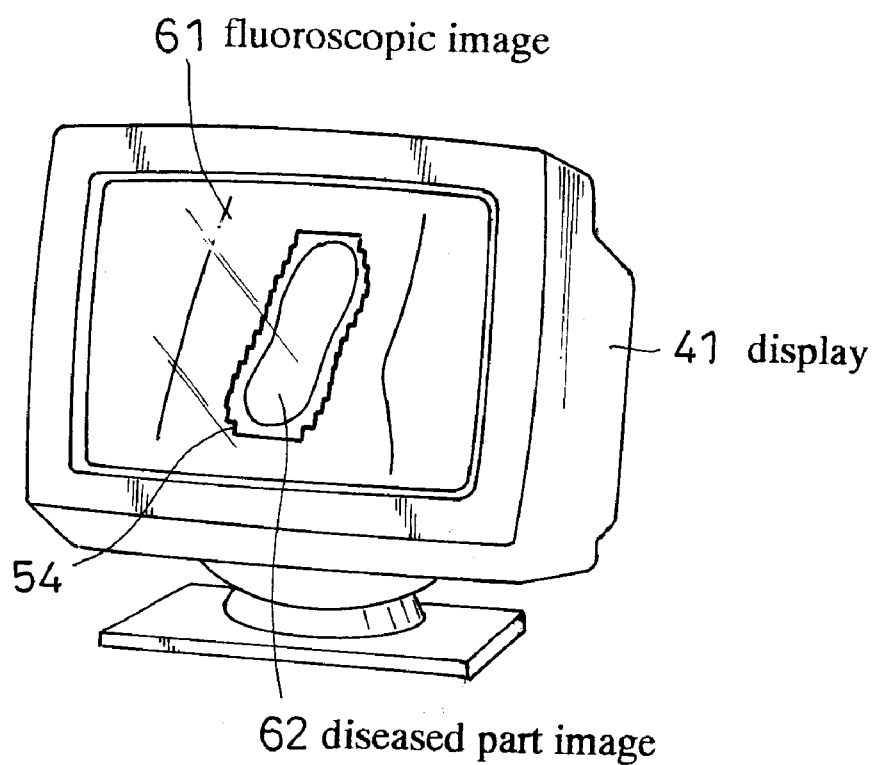
FIG. 6 is a perspective view of a display showing a fluoroscopic image with the field shape superposed thereon.

Next, the ring-shaped frame 24 is rotated to bring the irradiating direction of X-ray simulator 20 into agreement with the irradiating direction determined as described above. In this state, the X-ray tube 22 is driven to emit X rays. The X rays transmitted through the patient 32 are received by the flat panel imaging system for medical X ray 23 to acquire signals of a fluoroscopic image therefrom. The signals are transmitted to the computer 40. As shown in FIG. 6, a resulting fluoroscopic image 61 is displayed on the screen of display 41. An image of the diseased part 62 picked up by fluoroscopy appears on the screen. The field shape 54 also is displayed as superposed on the fluoroscopic image 61. Thus, the operator can verify suitability of the field shape 54 on the fluoroscopic image 61 taken from the same direction as the irradiating direction. The fluoroscopic image 61 is a dynamic image which enables the operator to check suitability of the field shape 54 even when the diseased part image 62 moves with respiration of the patient 32.

When found unsuitable as a result of such checking, the field shape 54 may be corrected on the screen (i.e. on the fluoroscopic image 61). The corrected field shape 54 may be confirmed on the screen by displaying the simulation image 52 again which is stored in the computer 40.

This construction allows the operator to verify the set field shape 54 and correct it into a suitable field shape on the fluoroscopic image 61 as necessary. The corrected field shape 54 may be superposed on the image (simulation image 52) acquired from the CT simulator 10. Thus, the corrected field shape 54 may be confirmed also on the image acquired from the CT simulator 10. In this way, the validity of field shape 54 may be verified with increased reliability.

Although it is desirable to provide the function to correct the field shape on the fluoroscopic image, and the function to display the corrected image as superposed on the image acquired from the CT simulator, these functions are not absolutely necessary.

Figure 7:
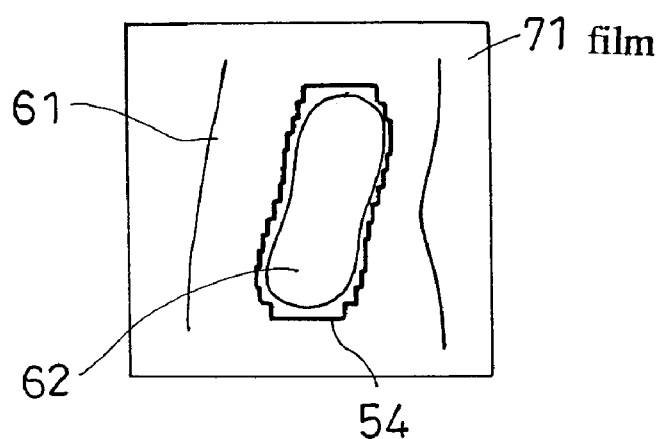
FIG. 7 is a view of a film showing the X-ray fluoroscopic image with the field shape superposed thereon.

Once the field shape 54 is finally determined, a selected frame of the fluoroscopic image 61 (including the field shape 54) displayed on the display 41 is printed on film 71 as shown in FIG. 7, by a laser printer or the like not shown. The film 71 shows the diseased part image 62 along with the fluoroscopic image 61 and field shape 54, and may therefore be used as a reference photograph for collation purposes.

In a conventional apparatus, an X-ray simulator takes a collating photograph with an X-ray tube and a film opposed to each other across a patient. A field shape is shown in the collating photograph by including therein a wire or the like representing the field shape. Consequently, the collating photograph reflects the field shape only in a rough form, and cannot present the field shape accurately. In this embodiment, on the other hand, the collating photograph showing the fluoroscopic image 61 and field shape 54 is obtained by using the computer 40 and laser printer or the like. This collating photograph presents the field shape accurately.

When a radiotherapy plan has been completed as described above, the patient 32 is set to a radiation treating apparatus not shown. At this time, the patient 32 is positioned by using the mark applied to the skin surface of the patient 32, so that the irradiating direction and isocenter of the radiation treating apparatus be in accord with the plan. In this radiation treating apparatus also, an irradiation field is set according to the plan. In this state, radiation is applied to the patient 32 for a short time with a film placed behind the patient 32, to photograph a transmitted image on the film. The transmitted image photographed on the film is collated with the reference photograph, to determine whether the patient 32 may actually be treated with radiation, with angles, isocenter and field shape as planned. After confirming that radiation may be applied as planned, radiation treatment is carried out by emitting radiation.

According to this embodiment, as described above, the flat panel imaging system for medical X ray 23 is used in the X-ray simulator 20 to acquire image signals of a fluoroscopic image. The fluoroscopic image 61 free from distortion may be displayed on the display 41, as distinct from using an image intensifier having a curved X-ray incidence plane causing an image distortion. This enables a proper verification of the validity of field shape 54 on the fluoroscopic image 61. Since the validity of field shape 54 is checked on the fluoroscopic image 61 displayed as a dynamic image, an appropriate field shape 54 may be determined even when the patient 32 has moved. In addition, the fluoroscopic image 61 is far superior in image quality to the simulation image 52. By using the fluoroscopic image 61, the field shape 54 may be confirmed and its suitability secured with ease.

The flat panel imaging system for medical X ray 23 has numerous small elements (corresponding to pixels) arranged on a flat panel for directly generating electric signals corresponding to intensities of incident X rays. The electric signals are read from these elements to output image signals. That is, the image signals representing a transmitted image provided by X-ray beams transmitted through the patient 32 are acquired directly. The flat panel imaging system for medical X ray 23 has a TFT (Thin Film Transistor) structure which is extremely thin and light. Therefore, without requiring a support structure of great strength, compared with a conventional combination of an image intensifier and a TV camera, fluoroscopic images may be picked up from varied angles with improved precision and with enhanced geometrical precision. This means that an irradiation field shape may be determined with increased accuracy and suitability though the construction is very simple and inexpensive.

Figure 8:
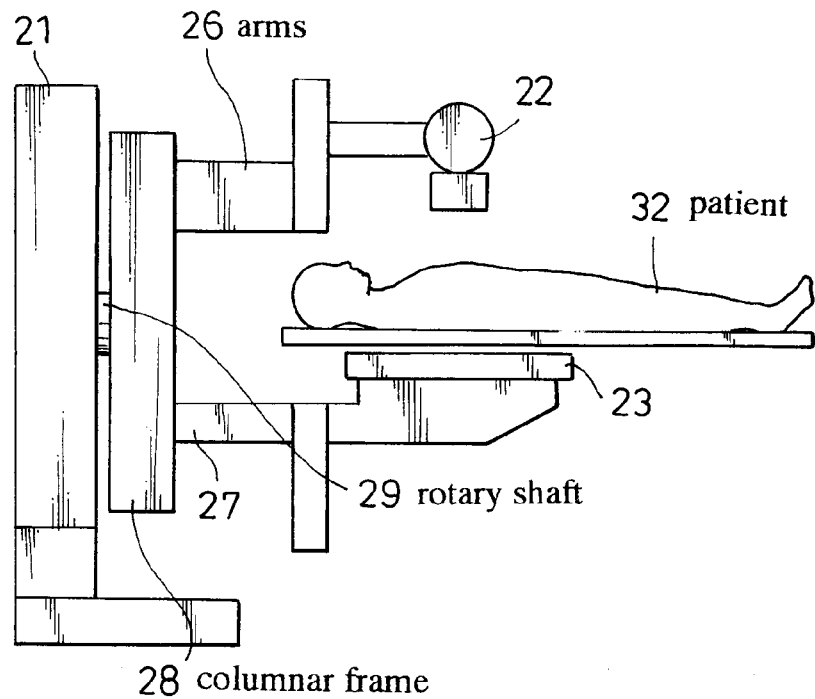
FIG. 8 is a side view of a modified X-ray simulator.
Figure 9:
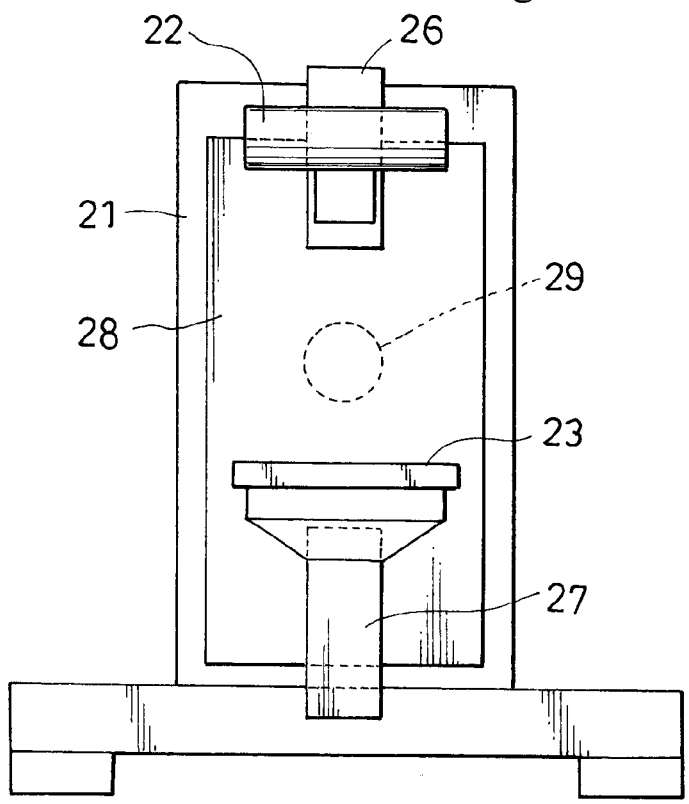
FIG. 9 is a front view of the modified X-ray simulator.

In the above embodiment, the X-ray simulator 20 uses the ring-shaped frame 24. As shown in FIGS. 8 and 9, a columnar frame 28 may be used instead. In this case, the columnar frame 28 is supported by the gantry 21 through a rotary shaft 29. The X-ray tube 22 and flat panel imaging system for medical X ray 23 are mounted on arms 26 and 27 of the columnar frame 28. With the columnar frame 28 rotated by the rotary shaft 29, the patient 32 is irradiated with X rays from selected directions, and image signals of fluoroscopic images are acquired from the flat panel imaging system for medical X ray 23.

In the foregoing embodiment, the bed table 30 is pivotable about the support axis 31 to be shared by the CT simulator 10 and X-ray simulator 20. Instead, separate bed tables may be provided individually. This achieves an increased freedom of equipment installation such that the CT simulator 10 and X-ray simulator 20 may be installed in separate rooms. In this case, however, the patient 32 must be moved between these bed tables. The patient 32 is set in position by using only the mark applied to the skin surface as a reference. Thus, the positioning must rely on a manual operation of the operator.

In the foregoing embodiment, numerous sectional images 51 are acquired from the CT simulator 10 to produce the simulation images 52 seen from particular directions. Without acquiring the sectional images, CR images seen from particular directions may be acquired directly as simulation images. In this case, the bed table 30 is moved while the X-ray tube XT and X-ray detector XS in the CT image pickup gantry 11 are fixed to a selected angle, to acquire transmitted images (CR images) taken in the irradiating direction.

In the foregoing embodiment, the images acquired from the CT simulator 10 and those acquired from the X-ray simulator 20 are processed by one computer 40. A treatment plan may be made efficiently while operating the one computer 40 to display the images acquired from the CT simulator 10 and X-ray simulator 20. Instead, separate computers may be provided for processing the images acquired from the CT simulator 10 and those acquired from the X-ray simulator 20.

Further, in the foregoing embodiment, the CT simulator 10 includes the projector 14 for emitting light in the field shape 54 to the patient 32. It is preferable but not essential to provide the projector. Similarly, it is preferable but not essential to provide the pointer 15 for the X-ray simulator 20.

The present invention may be embodied in other specific forms without departing from the spirit or essential attributes thereof and, accordingly, reference should be made to the appended claims, rather than to the foregoing specification, as indicating the scope of the invention.

What is claimed is:

1. A radiotherapy planning system for making a treatment plan for radiation treatment, comprising:

a CT simulator including a CT image pickup gantry having an X-ray tube and X-ray detecting means, a pointer for indicating an irradiation center, and patient support means;

an X-ray simulator including an X-ray tube, a flat panel imaging system for medical X ray, and patient support means;

setting means for setting an irradiation field shape and an irradiation center on an image acquired from said CT simulator; and superposing and displaying means for displaying a fluoroscopic image acquired from said X-ray simulator, with said irradiation field shape superposed thereon.

2. A radiotherapy planning system as defined in claim 1, wherein said setting means and said superposing and displaying means comprise a computer.

3. A radiotherapy planning system as defined in claim 1, wherein images acquired from said CT simulator and images acquired from said X-ray simulator are processed by one computer.

4. A radiotherapy planning system as defined in claim 1, wherein one patient support means acts as said patient support means of said CT simulator and said patient support means of said X-ray simulator.

5. A radiotherapy planning system as defined in claim 4, wherein said CT simulator and said X-ray simulator are arranged around said one patient support means, said one patient support means being pivotable about a support axis.

6. A radiotherapy planning system as defined in claim 1, wherein said patient support means of said CT simulator and said patient support means of said X-ray simulator are separate.

7. A radiotherapy planning system as defined in claim 1, wherein said CT simulator further includes projecting means for emitting to a patient light of said irradiation field shape set by said setting means.

8. A radiotherapy planning system as defined in claim 1, wherein said X-ray simulator further includes a pointer for indicating an irradiation center.

9. A radiotherapy planning system as defined in claim 1, further comprising correcting means for correcting said irradiation field shape set by said setting means, on said fluoroscopic image acquired from said X-ray simulator.

10. A radiotherapy planning system as defined in claim 9, further comprising confirmation-aiding superposing and displaying means for displaying said fluoroscopic image acquired from said X-ray simulator, with, superposed thereon, said irradiation field shape corrected by said correcting means.

11. A radiotherapy planning system as defined in claim 9, wherein said correcting means comprises a computer.

12. A radiotherapy planning system as defined in claim 10, wherein said confirmation-aiding superposing and displaying means comprises a computer.

* * * * *